(12) United States Patent
Kim et al.

(10) Patent No.: US 8,776,463 B2
(45) Date of Patent: Jul. 15, 2014

(54) VIBRATION ISOLATOR OF WIND TURBINE SYSTEM

(75) Inventors: Bong-Suk Kim, Suwon-si (KR); Man-Eok Hur, Seoul (KR); Joon-Keun Lee, Seoul (KR)

(73) Assignee: LS Cable & Systems Ltd., Anyang-si, Gyeonggi-do (KR)

( * ) Notice: Subject to any disclaimer, the term of this patent is extended or adjusted under 35 U.S.C. 154(b) by 0 days.

(21) Appl. No.: 13/641,228

(22) PCT Filed: Apr. 14, 2011

(86) PCT No.: PCT/KR2011/002665
§ 371 (c)(1),
(2), (4) Date: Oct. 15, 2012

(87) PCT Pub. No.: WO2011/129629
PCT Pub. Date: Oct. 20, 2011

(65) Prior Publication Data
US 2013/0031859 A1 Feb. 7, 2013

(30) Foreign Application Priority Data

Apr. 15, 2010 (KR) .................. 10-2010-0034706

(51) Int. Cl.
*E02D 27/00* (2006.01)
(52) U.S. Cl.
USPC .............................................. 52/295; 52/296

(58) Field of Classification Search
USPC .................. 52/295, 296, 167.1, 167.2, 167.7, 52/167.8, 848
See application file for complete search history.

(56) References Cited

U.S. PATENT DOCUMENTS

| | | | | |
|---|---|---|---|---|
| 2,888,779 | A | * | 6/1959 | Hostetter ........................... 47/33 |
| 4,830,927 | A | * | 5/1989 | Fukahori et al. .............. 428/495 |
| 4,887,788 | A | * | 12/1989 | Fischer et al. ................. 248/562 |
| 4,899,323 | A | * | 2/1990 | Fukahori et al. .............. 367/176 |
| 5,797,228 | A | * | 8/1998 | Kemeny ....................... 52/167.7 |
| 6,385,918 | B1 | * | 5/2002 | Robinson ..................... 52/167.8 |
| 7,805,895 | B2 | * | 10/2010 | Kristensen ................... 52/169.9 |
| 7,856,766 | B2 | * | 12/2010 | Takenoshita et al. ........ 52/167.8 |
| 8,220,214 | B1 | * | 7/2012 | Purdy ............................. 52/296 |
| 8,359,798 | B2 | * | 1/2013 | Armbrecht et al. ............ 52/297 |
| 2002/0035808 | A1 | * | 3/2002 | Orovay et al. ............... 52/167.8 |
| 2008/0222975 | A1 | * | 9/2008 | Nakata et al. ................ 52/167.9 |
| 2009/0313917 | A1 | * | 12/2009 | Takenoshita et al. ........ 52/167.7 |

FOREIGN PATENT DOCUMENTS

DE     298 06 010 U1    6/1998

\* cited by examiner

*Primary Examiner* — Basil Katcheves
(74) *Attorney, Agent, or Firm* — Sherr & Jiang, PLLC

(57) ABSTRACT

A vibration isolator of a wind turbine system installed between a wind tower and a concrete foundation includes a plurality of bearing units arranged along the periphery of a flange of the wind tower, each bearing unit having elastic material layers and rigid material layers stacked alternately.

13 Claims, 5 Drawing Sheets

(a)

(b)

VIBRATION ISOLATOR OF WIND TURBINE SYSTEM

TECHNICAL FIELD

The present invention relates to a vibration isolator, and more particularly, to a vibration isolator of a wind turbine system which is installed between a wind tower of the wind turbine system and a foundation under the wind tower.

BACKGROUND ART

Cross-Reference to Related Application

This application claims priority to Korean Patent Application No. 10-2010-0034706 filed in the Republic of Korea on Apr. 15, 2010, the entire contents of which are incorporated herein by reference.

A wind tower is a structure that supports blades, a hub, and a nacelle, wherein a gearbox, a generator, and the like are assembled in the nacelle, and a typical wind tower currently used for a wind turbine of a large wind turbine system has a tubular structure.

The wind tower is configured to resist thrust generated by the rotation of the blades, self-weight by the mass of the nacelle and the blades, wind load, and the like. The wind tower is liable to suffer a large loss caused by breakage, and because the wind tower is a high-cost component occupying about 20 to 25% of the cost of a large wind turbine, it is important to ensure the safety of the wind tower.

The wind tower may be made from woods, composite materials, steel, concrete, steel/concrete mixtures, and the like, and among them, steel is most widely used. Typically, a steel wind tower is manufactured such that a plurality of conical shells are welded to a flange, which is known as a shell-type wind tower. Although the wind tower is made from a steel material, when the wind tower increases in size, the wind tower is more likely to be affected by an external environment such as a gust of wind and the like, and in some instances, the wind tower may be broken or destroyed.

The main load and an external force that should be taken into consideration in the wind turbine system are an earthquake vibration transmitting from the concrete foundation, a wind load affecting the structural stability of the system more intensively with an increase in height of the wind tower, a rotary power resulting from the rotation of the blades, and the like. The load and the external force may often cause unfavorable vibrations to the wind tower based on dynamic characteristics of the wind tower such as a natural frequency, a mode type or damping effect, mass, rigidity, a slenderness/aspect ratio, and the like, resulting in critical consequences. The wind load and the gust of wind that are transmitted in various directions acting as a horizontal load have a high slenderness/aspect ratio and a low damping ratio, and thus leads to a problem of a great dynamic response (horizontal displacement and acceleration response) effect caused by a variable wind velocity component.

However, the conventional wind turbine system is only installed so that the wind tower is securely supported by welding the bottom of the wind tower to the concrete foundation through the flange and engaging them by a bolt, regardless of a wind load and the like. As a result, the conventional wind turbine system does not effectively react to a dynamic load such as an earthquake load or a wind load, and in some instances, the wind tower may be broken or destroyed.

To react to a dynamic load applied to the wind tower, suggestions have been made to support the wind tower using a vibration isolator. The vibration isolator is disclosed in, for example, Korean Patent Publication Nos. 1997-0705712, 1990-0018482, and 2009-0089629.

As shown in FIG. 1, the conventional vibration isolator includes an elastic body having inner rubber layers 13 and reinforcing steel plates 12 stacked alternately and a rubber cover 11 surrounding the stack, a lead core 10 penetrating the elastic body, and a flange 14 attached to the bottom of the elastic body for mounting the wind tower. The vibration isolator of this structure is generally known as a 'lead rubber bearing (LRB)'.

When an earthquake occurs, the LRB isolates the earthquake vibration by shear de-formation of the inner rubber layers 13 having elastic properties to artificially increase a natural frequency of the wind tower, and when the vibration disappears, the LRB restores to its original shape by an elastic force.

The LRB has sufficient rigidity due to the reinforcing steel plates 12 interposed between the inner rubber layers 13, and thus provides resistance and stability to a vertical load.

The lead core 10 of the LRB is configured to reinforce the energy absorbing capability of the inner rubber layers 13 and to reduce deformation of the inner rubber layers 13. When it comes to load forms that are applied gradually over a long time like the temp load, the LRB easily yields using the creep characteristic of the lead core and transmits the temp load to its surrounding by a small amount. Also, the LRB resists, with great rigidity, a load applied for a short time like a wind load.

When the conventional LRB is used under a high wind load environment, the lead core 10 needs to have an increased installation area in the LRB to improve its resistance effect, however this may decrease an elastic restoring force of the elastic body and give rise to an environmental problem caused by the use of a large amount of lead.

In particular, unlike building structures, the wind tower structure has a much larger vertical length than width, and subject to temperature changes of the season and daily temperature ranges, great temperature elasticity can occur. When the wind tower structure does not provide a proper response to the temperature elasticity problem, the wind tower structure may suffer severely from temperature stresses.

The conventional LRB is mainly designed to resist a wind load for structures having a large horizontal length like that of bridges, and when the LRB of such design is applied to a wind tower, the wind tower has low resistance to a vertical load and is difficult to damp vibration by a wind load or a blade thrust. Accordingly, there is an urgent need for the development of a vibration isolator of a wind turbine system.

DISCLOSURE OF INVENTION

Technical Problem

The present invention is designed to solve the above-mentioned problems, and therefore it is an object of the present invention to provide a vibration isolator of a wind turbine system which may minimize an amount of lead core and provide resistance to vertical and horizontal loads suitable for a wind turbine system.

It is another object of the present invention to provide a vibration isolator of a wind turbine system which may have a lead core arrangement to improve resistance to a horizontal load.

It is still another object of the present invention to provide a vibration isolator of a wind turbine system which may decrease friction between an inner rubber layer and a reinforcing plate to reduce shear stresses.

Solution to Problem

To achieve the objects, the present invention provides a vibration isolator of a wind turbine system installed between a wind tower and a concrete foundation, including a plurality of bearing units arranged along the periphery of a flange of the wind tower, each bearing unit having elastic material layers and rigid material layers stacked alternately.

The bearing unit may further have a core member penetrating a stack of the elastic material layers and the rigid material layers.

The plurality of bearing units may be arranged to form a circle as a whole, and the bearing unit may have at least two core members spaced away from each other in a radial direction of the circle, and the core member near an outer periphery of the circle may be made from a material of better vibration isolation performance than the core member near an inner periphery.

The core member may be made from any one selected from a group consisting of Pb, Sn, Zn, and Al.

The core members may be arranged at the middle point in a length direction of the bearing unit.

Alternatively, the core members may be arranged at four edges of the bearing unit.

The core member may have a bolt shape and may be screwed in the stack of the elastic material layers and the rigid material layers.

Preferably, the plurality of bearing units may be arranged to form a circle as a whole, and adjacent bearing units may be engaged to each other by a combination of concave and convex portions.

Preferably, a gap may be formed between the adjacent bearing units.

The width of the gap may be smaller than the depth of the concave portion or the height of the convex portion.

Preferably, the gap may have a larger width along the outer periphery than the width along the inner periphery.

The elastic material layers may be made from rubber, and the rigid material layers may be made from metal.

The bearing unit may further have an elastic material cover surrounding the bearing unit.

According to another aspect of the present invention, a bearing unit of a vibration isolator of a wind turbine system, which is positioned along the periphery of a flange of a wind tower between the wind tower and a foundation, including a unit body having elastic material layers and rigid material layers stacked alternately, a core member penetrating a stack of the elastic material layers and the rigid material layers, and an elastic material cover surrounding the stack of the elastic material layers and the rigid material layers, and a concave portion and a convex portion are formed at the opposing sides in a length direction of the unit body, the convex portion having a contour matched to the concave portion.

Advantageous Effects of Invention

A vibration isolator of a wind turbine system according to the present invention provides the following effects.

First, the vibration isolator has a plurality of bearing units arranged along the periphery of a flange of a wind tower and engaged to each other by a combination of concave and convex portions, and thus provides vibration isolation characteristics suitable for an environment where an external force of variable directionality is applied. The bearing units have a gap therebetween, which enables the vibration isolator to implement self-alignment at or after the action of the external force.

Second, the vibration isolator has a bolt-type core member inserted into the bearing unit to provide an energy absorbing function. The core member helps to stably maintain a stack of the elastic material layers and the rigid material layers and to securely install the bearing unit against the flange of the wind tower.

Third, the vibration isolator may have a hybrid-type core member positioned in a radial direction, so that the vibration isolator may effectively isolate a horizontal load applied to the wind tower by a gust of wind and the like, and may minimize or eliminate the use of lead, thereby reducing the environmental pollution.

BRIEF DESCRIPTION OF DRAWINGS

The accompanying drawings illustrate the preferred embodiments of the present invention and are included to provide a further understanding of the spirit and scope of the present invention together with the detailed description of the invention, and accordingly, the present invention should not be limitedly interpreted to the matters shown in the drawings.

BEST MODE FOR CARRYING OUT THE INVENTION

Hereinafter, the present invention will be described in detail with reference to the accompanying drawings. Prior to the description, it should be understood that the terms used in the specification and appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Figure 1:
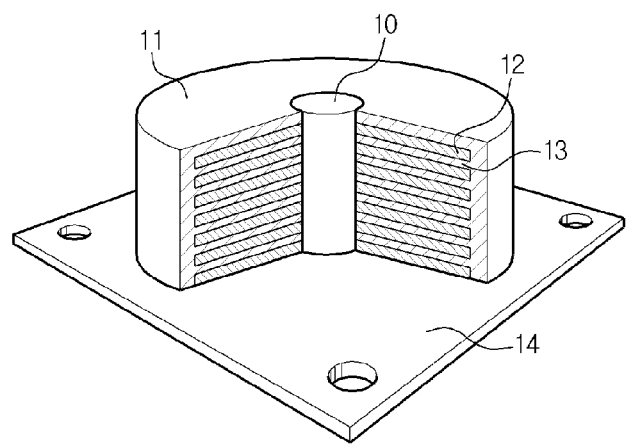
FIG. 1 is a partial cut-away perspective view illustrating a structure of a conventional vibration isolator.
Figure 1:
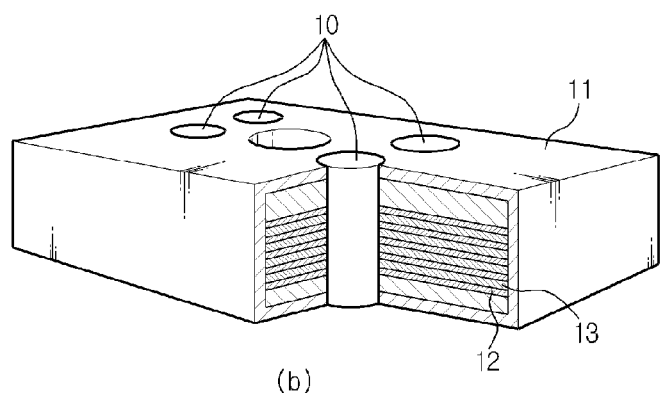
Figure 2:
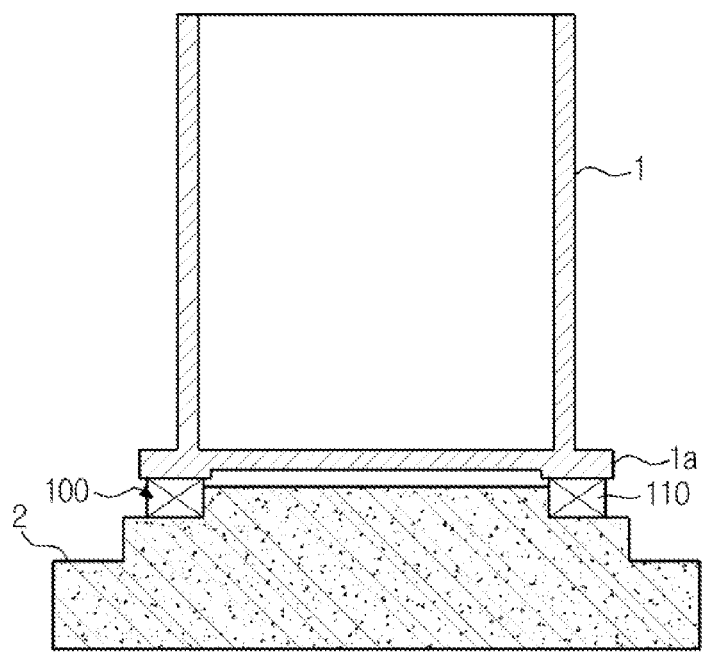
FIG. 2 is a cross-sectional view illustrating an installation example of a vibration isolator of a wind turbine system according to a preferred embodiment of the present invention.

FIG. 2 is a schematic cross-sectional view illustrating an installation example of a vibration isolator 100 for a wind tower 1 according to a preferred embodiment of the present invention. As shown in FIG. 2, the vibration isolator 100 according to a preferred embodiment of the present invention is installed between a flange 1a of the wind tower 1 and a concrete foundation 2. Although not shown in FIG. 2, the flange 1a of the wind tower 1 and a concrete foundation 2 are engaged to each other by a bolt.

Figure 3:
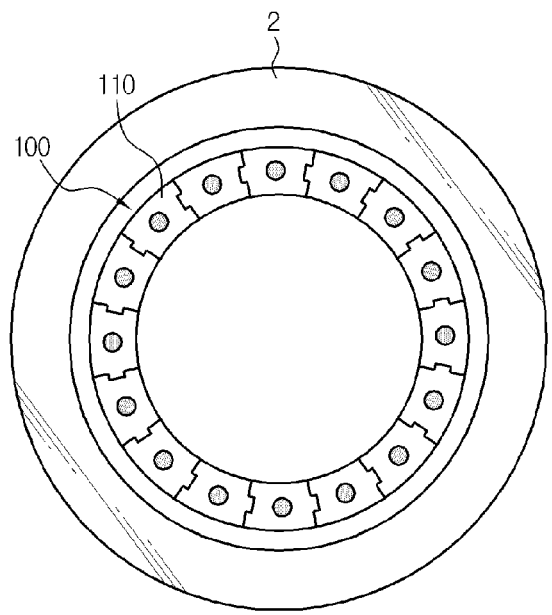
FIG. 3 is a top view illustrating an array of bearing units of FIG. 2.
Figure 12:
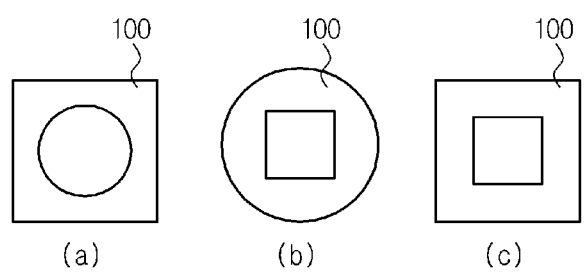
FIG. 12 is a schematic top view illustrating available arrangements of bearing units according to the present invention.

As shown in FIG. 3, the vibration isolator 100 according to a preferred embodiment of the present invention has a plurality of bearing units 110 assembled in a chain along the periphery of the flange 1a of the wind tower 1. Preferably, the plurality of bearing units 110 are arranged in the shape of a circle as a whole such that adjacent bearing units 110 are engaged to each other by a combination of concave and convex portions. Alternatively, the plurality of bearing units 110 may be arranged in various shapes along the periphery of the wind tower, as shown in FIG. 12.

This feature of the bearing units 110 assuming the whole shape of a circle and being engaged to each other by a combination of concave and convex portions as described above enables the wind tower 1 to effectively resist a vertical load, and to effectively damp an external force of variable directionality resulting from thrust generated by the rotation of blades equipped in the wind tower 1, self-weight by the mass of a nacelle and the blades, wind load, and the like.

The bearing units 110 engaged to each other by a combination of concave and convex portions may have a gap therebetween. The gap enables the bearing units 110 to maintain a stable state through self-alignment at or after the action of the external force.

Figure 4:
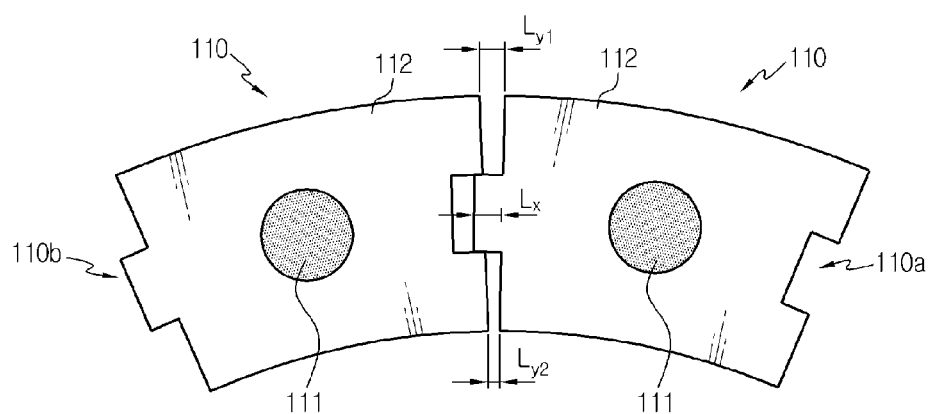
FIG. 4 is a partial top view illustrating a gap between concave and convex portions of the bearing units of FIG. 3.

FIG. 4 illustrates the relationship in size between the gap formed between the bearing units 110, and concave and convex portions. The gap between the bearing units 110 has widths $L_{y1}$ and $L_{y2}$ smaller than a depth of a concave portion 110a or a height $L_x$ of a convex portion 110b. Also, the width $L_{y1}$ of the gap along an outer periphery of the circle formed by the bearing units 110 is larger than the width $L_{y2}$ of the gap along an inner periphery. This configuration may ensure a sufficient space for self-alignment of the bearing units 110, because an area around the outer periphery is subject to a larger load than an area around the inner periphery due to a circular arrangement of the bearing units 110.

Figure 5:
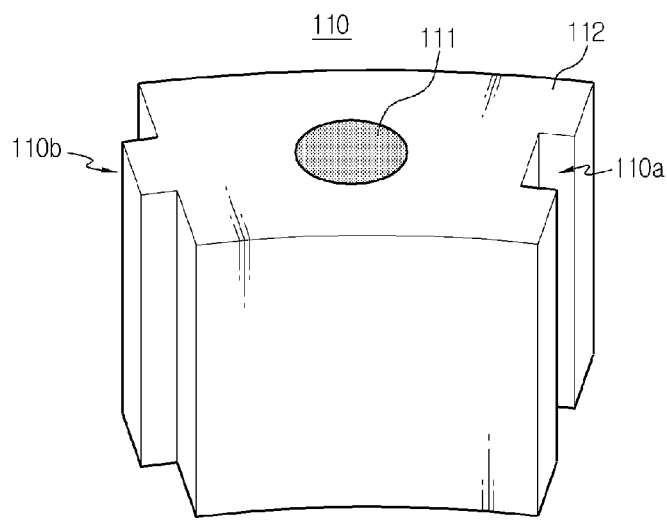
FIG. 5 is a perspective view illustrating the bearing unit of FIG. 3.
Figure 6:
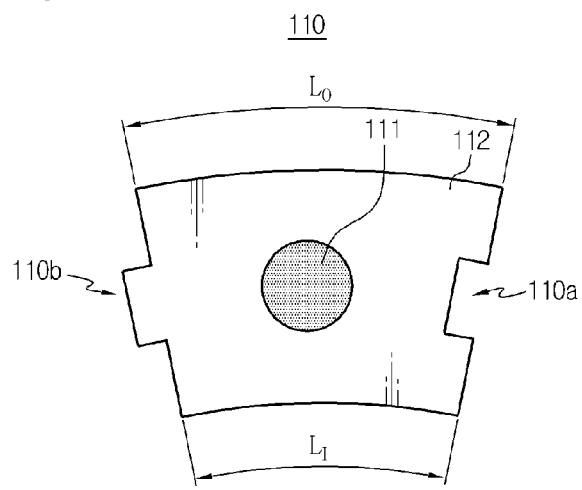
FIG. 6 is a top view of FIG. 5.

As shown in FIGS. 5 and 6, the bearing unit 110 comprises a unit body having curved portions at the opposing sides in a width direction and a concave portion 110a and a convex portion 110b at the opposing sides in a length direction, and the convex portion has a contour matched to the concave portion 110a.

When the bearing units 110 are arranged in the shape of a circle as described above, the length $L_o$ of an outer arc is larger than the length $L_1$ of an inner arc, the outer arc extending along the outer periphery of the circle when the bearing units 110 are assembled.

At least one core member 111 may be inserted in the unit body of the bearing unit 110 to absorb and damp a load of the wind tower 1. Preferably, the core member 11 may be made from any one selected from the group consisting of Pb, Sn, Zn and Al, or combinations thereof. However, the present invention is not limited in this regard, and a variety of modified embodiments may be implemented.

Figure 7:
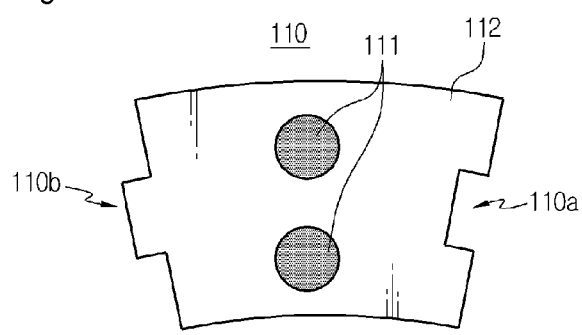
FIGS. 7 to 9 are top views illustrating variation examples of FIG. 5.

Based on the fact that an area around the outer periphery is subject to a larger load than an area around the inner periphery, at least two core members 111 may be provided at the middle point in the length direction of the bearing unit 110, and the core members 111 may be spaced away from each other in a radial direction of the circle, as shown in FIG. 7. In this instance, the core member 111 near the outer periphery may be preferably made from a material having better vibration isolation performance such as energy absorbing capability, damping capability, yielding capability, and resistance to a horizontal load, than the core member 111 near the inner periphery. For example, the core member 111 near the outer periphery may be made from Zn and the core member 111 near the inner periphery may be made from Sn or Pb. The hybrid-type core member 111 made from both Pb and a material other than Pb has an advantage of a reduction in environmental pollution caused by the use of Pb. Alternatively, the use of Pb may be eliminated, and the core member 111 may be made from Sn, Zn, Al, and the like.

Figure 8:
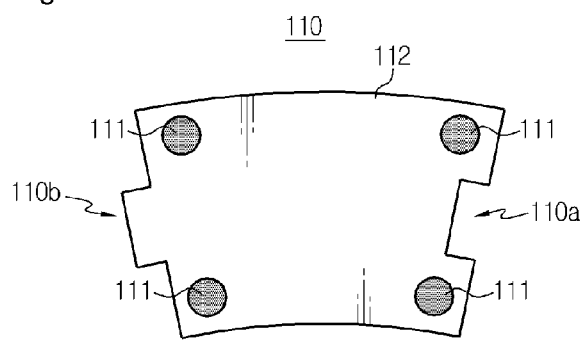

The core member 111 may be located at four edges of the unit body of the bearing unit 110, as shown in FIG. 8. In this case, the core members 111 at the four edges of the bearing unit 110 may be made from the same material, and as described above, the core members 111 near the outer periphery and the core members 111 near the inner periphery may be made from different materials to provide different energy absorbing capabilities, damping capabilities, yielding capabilities, and resistance to a horizontal load.

Figure 9:
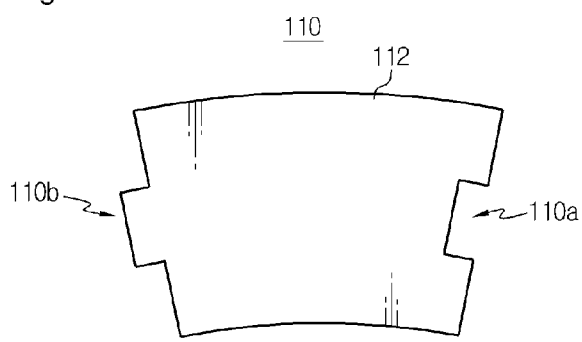
Figure 11:
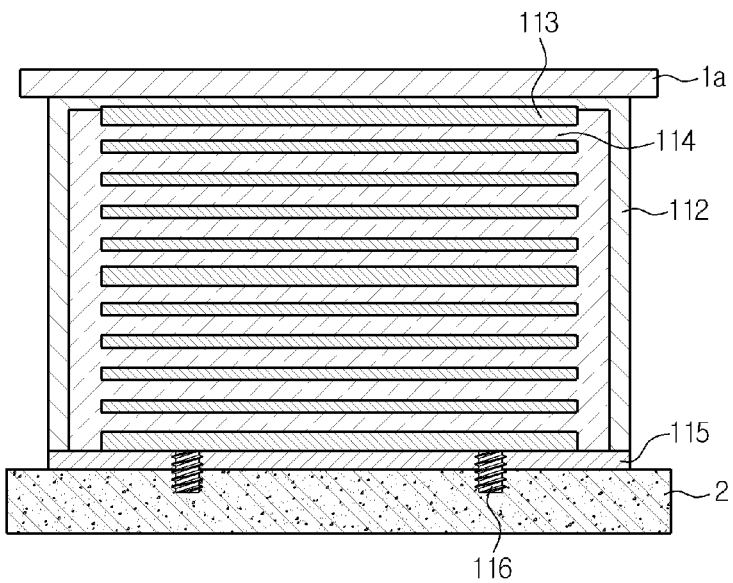
FIG. 11 is a cross-sectional view illustrating an internal structure of a bearing unit according to another embodiment of the present invention.

The bearing unit 110 free of a core member according to another embodiment of the present invention may be provided, as shown in FIGS. 9 and 11.

Figure 10:
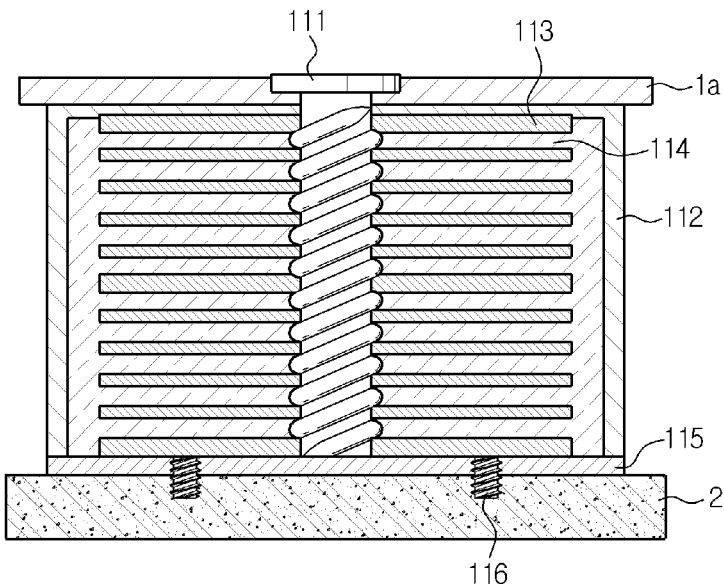
FIG. 10 is a cross-sectional view illustrating an internal structure of a bearing unit according to an embodiment of the present invention.

FIG. 10 is a cross-sectional view illustrating an internal structure of the bearing unit 110. As shown in FIG. 10, the bearing unit 110 has elastic material layers 114 and rigid material layers 113 stacked alternately, an elastic material cover 112 surrounding the stack of the elastic material layers 114 and the rigid material layers 113, and a bolt-type core member 111 penetrating the stack of the elastic material layers 114 and the rigid material layers 113.

Preferably, the rigid material layers 113 of the bearing unit 110 are formed of metal plates, and the elastic material layers 114 are formed of rubber plates interposed between the rigid material layers 113.

The rigid material layers 113 are configured to reinforce resistance to a vertical load ensured by the elastic material layers 114. The thickness of the rigid material layer 113 should be selected based on variable ambient vibrations or earthquake vibrations, wind loads including a gust of wind, and the like.

A screw hole (not shown) is formed in the center of the stack of the elastic material layers 114 and the rigid material layers 113, and the core member 111 is engaged in the screw hole.

As described above, the core member 111 is configured to absorb and damp a load of the wind tower 1. In particular, a bolt-type core member made from Pb may be plastically deformed and collapsed by a horizontal load and the like. Accordingly, the core member 111 should have an elastic range, a ratio of height to diameter in a bolt body, damp displacement, a horizontal load, horizontal displacement characteristics, and the like, that are optimized within such a range not to bring about plastic deformation.

The elastic material cover 112 which surrounds the stack of the elastic material layers 114 and the rigid material layers 113 is used to keep the external shape and protect the internal components, and is preferably made from rubber. Preferably, the elastic material cover 112 is integrally formed with the elastic material layers 114.

When the bearing units 110 are installed in the wind tower 1, the upper portion of the elastic material cover 112 is closely contacted with the lower surface of the flange 1a of the wind tower 1, and the core member 111 is inserted from the upper portion of the flange 1a toward the elastic material cover 112 and is engaged through the stack of the elastic material layers 114 and the rigid material layers 113. For this purpose, the flange 1a of the wind tower 1 may have a groove for receiving a bolt head of the core member 111 on the upper surface thereof.

The bearing unit 110 has a steel plate 115 for supporting the bearing unit 110 at the bottom thereof. A steel bolt 116 is fastened into the steel plate 115 to fix the bearing unit 110 in the concrete foundation 2.

The vibration isolator 100 having the above-mentioned structure according to a preferred embodiment of the present invention is installed between the flange 1a of the wind tower 1 and the concrete foundation 2 to perform a vibration isolation function in applications including a vertical load, a horizontal load, a wind load, a blade thrust, and the like.

The vibration isolator 100 according to a preferred embodiment of the present invention has a plurality of bearing units 110 arranged along the periphery of the wind tower 1 and engaged by a combination of concave and convex portions. Accordingly, the vibration isolator 100 may provide vibration isolation characteristics suitable to the wind tower 1 placed under an environment where an external force of variable directionality may shake in all directions.

In the vibration isolator 100, a gap is formed between concave and convex portions of adjacent bearing units 110, and enables the bearing units 110 to implement self-alignment at or after the action of the external force, thereby maintaining a structurally stable arrangement.

Hereinabove, the present invention is described in detail with reference to the accompanying drawings. However, the description proposed herein is just a preferable example for the purpose of illustrations only, not intended to limit the scope of the invention, so it should be understood that other equivalents and modifications could be made thereto without departing from the spirit and scope of the invention.

Industrial Applicability

The present invention may effectively damp a vertical load, a horizontal load, a wind load, a blade thrust, and the like, that are applied to a wind tower, to protect a wind turbine system.

The invention claimed is:

1. A vibration isolator of a wind turbine system, the vibration isolator comprising:
   a plurality of bearing units installed between a wind tower and a concrete bottom base and arranged along the periphery of a flange of the wind tower, each bearing unit having elastic material layers and rigid material layers stacked alternately,
   wherein the plurality of bearing units are arranged to form a circle,
   wherein adjacent bearing units are engaged to each other by a combination of concave and convex portions, and
   wherein the adjacent bearing units are engaged to each other to form a gap therebetween.

2. The vibration isolator of wind turbine system according to claim 1, wherein the bearing unit further has a core member penetrating a stack of the elastic material layers and the rigid material layers.

3. The vibration isolator of wind turbine system according to claim 2,
   wherein the bearing unit has at least two core members spaced away from each other in a radial direction of the periphery.

4. The vibration isolator of wind turbine system according to claim 2, wherein the core member is made from any one selected from a group consisting of Pb, Sn, Zn, and Al.

5. The vibration isolator of wind turbine system according to claim 2, wherein the core member has a bolt shape and is screwed in the stack of the elastic material layers and the rigid material layers.

6. The vibration isolator of wind turbine system according to claim 1, wherein the width of the gap is smaller than the depth of the concave portion or the height of the convex portion.

7. The vibration isolator of wind turbine system according to claim 6, wherein the gap has a larger width along the outer periphery than a width along the inner periphery.

8. The vibration isolator of wind turbine system according to claim 1, wherein the elastic material layers are made from rubber, and the rigid material layers are made from metal.

9. The vibration isolator of wind turbine system according to claim 1, wherein the bearing unit further has an elastic material cover surrounding the bearing unit.

10. The vibration isolator of wind turbine system of claim 1, wherein the concave portion is formed at a first flat side surface of each bearing unit and the convex portion is formed at a second flat side surface of each bearing unit which is opposite to the first flat side surface, wherein the gap is formed between the concave portion and the convex portion and between adjacent first and second flat side surfaces of adjacent bearing units.

11. The vibration isolator of wind turbine system of claim 10, wherein the concave and convex portions are formed along a central portion of the flat side surface when viewed from a top of each bearing unit.

12. The vibration isolator of wind turbine system of claim 1, wherein the concrete bottom base includes a cylindrical protrusion and the plurality of bearing units are arranged to surround the cylindrical protrusion.

13. The vibration isolator of wind turbine system of claim 1, wherein the gap is configured to secure a clearance between adjacent bearing units so that each bearing unit is able to be self-aligned in a direction substantially perpendicular to a radial direction of the circle when an external force is applied.

* * * * *